(12) United States Patent  (10) Patent No.: US 7,470,026 B2
Kaido et al.  (45) Date of Patent: Dec. 30, 2008

(54) METHOD AND APPARATUS FOR MEASURING OPERATING VISUAL ACUITY

(75) Inventors: Minako Kaido, 1-22-1-1706, Ginza, Chuo-ku, Tokyo (JP); Kazuo Tsubota, Chiba-ken (JP)

(73) Assignees: Minako Kaido, Tokyo (JP); Qualitas Inc., Tokyo (JP)

( * ) Notice: Subject to any disclaimer, the term of this patent is extended or adjusted under 35 U.S.C. 154(b) by 367 days.

(21) Appl. No.: 11/482,845

(22) Filed: Jul. 7, 2006

(65) Prior Publication Data

US 2007/0008492 A1 Jan. 11, 2007

(30) Foreign Application Priority Data

Jul. 7, 2005 (JP) ............... 2005-198530

(51) Int. Cl.
*A61B 3/02* (2006.01)
*A61B 3/00* (2006.01)
(52) U.S. Cl. .............. 351/223; 351/222; 351/237; 351/200; 351/246; 351/239
(58) Field of Classification Search ......... 351/200, 351/205, 222, 223, 237–239, 246
See application file for complete search history.

(56) References Cited

U.S. PATENT DOCUMENTS 3,905,688 A 9/1975 Decker et al.
5,825,460 A 10/1998 Kohayakawa
7,393,104 B2 * 7/2008 Hara et al. ............ 351/239

FOREIGN PATENT DOCUMENTS

EP 1138251 A1 10/2001
JP 2001-309887 A 11/2001
WO WO 9200037 A1 1/1992

OTHER PUBLICATIONS

Krakau et al., "An automatic apparatus for time series analysis of visual acuity," Vision Research, Pergamon Press (Oxford, GB), (vol. 7), (Issue. 1-2), (p. 99-105), (Jan. 1967).

* cited by examiner

*Primary Examiner*—William C Choi
*Assistant Examiner*—Jack Dinh
(74) *Attorney, Agent, or Firm*—Hammer & Associates, P.C.

(57) ABSTRACT

The present invention provides a method and apparatus for measuring operating vision. An optotype mark is displayed (step 103). A subject's response to the optotype mark is accepted via an input device (step 104). A determination is made as to whether or not the response is correct (step 105). When the current response of the subject is correct and the previous response or one of the previous response and the last-but-one response is incorrect, an optotype mark corresponding to the same visual acuity is presented (step 112). When the previous response is correct or both the previous response and the last-but-one response are correct, an optotype mark corresponding to a visual acuity one level higher is presented (step 110). When the current response is incorrect, an optotype mark corresponding to a visual acuity one level lower is presented (step 111).

4 Claims, 5 Drawing Sheets

METHOD AND APPARATUS FOR MEASURING OPERATING VISUAL ACUITY

BACKGROUND OF THE INVENTION

1. Field of the Invention

The present invention generally relates to methods and apparatuses for measuring vision or visual acuity and methods for analyzing the same. More specifically, the present invention relates to a method for the measurement of so-called "operating vision" or "operating visual acuity" and to a method for analyzing vision.

2. Description of the Related Art

Conventional visual-acuity measurement instruments are designed to measure vision at the time of measurement under stress-free conditions that may be quite different from our day-to-day stressful conditions. Vision, however, declines through continuous use of the eyes. For some people, vision degrades rapidly after staring at a book, a video screen, or the like for a certain period of time without blinking. For example, staring without blinking while driving on an expressway may involve the risk of deteriorating vision. In some people, vision may drop under such conditions from about 1.0 to about 0.3. It is known that such a tendency is strong among people suffering from so-called "dry eye", in which the ocular surfaces tend to become dry. Thus, the vision measured with such a conventional visual-acuity measurement instrument, and the actual visual acuity when the eyes are experiencing stress (we refer to this type of visual acuity as "operating vision") may be different from each other, and the difference varies considerably depending on the individual and also on the environment and the degree of stress. In other words, with a temporary or momentary vision alone, it is difficult to accurately measure a subject's operating vision which is the effective vision the subject can utilize. In light of this tendency for vision to decline due to staring and also in view of influences of diseases, such as dry eye, on vision a person can practically use, it is desirable to measure deteriorating vision over time.

An apparatus for measuring operating vision is disclosed in JP 2001-309887 A. Such a known apparatus has been put into practical use. However, some points to be improved have also become apparent.

For example, with a conventional apparatus, if the subject's response to a newly displayed optotype mark is correct, a smaller optotype mark is presented, and if the response is incorrect, a larger optotype mark is presented (see paragraph No. 0017 in JP 2001-309887 A mentioned above). The method disclosed in this document is based on the premise that blinking is involved and the operating vision is recovered by blinking, as shown in FIG. 2 of JP 2001-309887 A. In actual tests, however, the eye is forcibly kept open, for example, for about 30 to 60 seconds in order to accurately measure the operating vision. Further, based on the premise that the operating vision decreases during the eye examination, a larger optotype mark is presented when an erroneous response is received, and optotype marks corresponding to the same vision are continuously presented when correct responses (i.e., correct answers) are continuously received.

Based on the premise that the operating vision decreases over time, a smaller optotype mark is not presented even when a correct response is received. This is because the operating vision measurement instruments were initially developed based on the assumptions that tear layers on the ocular surfaces deteriorate over time and measured visual acuity decreases over time. Thus, assuming that tear layers deteriorate unless blinking is allowed and the visual acuity tend to decrease over time, early operating vision measurement instruments were designed to display a larger optotype mark, which is to be read by the subject, for a visual acuity value which is for one level lower than the current vision level when the answer from the subject is incorrect or when no answer is given, and display an optotype mark corresponding to the same visual acuity value when the answer is correct.

Such an approach is reasonable if the eye is forcibly kept open. However, it has also become clear that subjects feel very uncomfortable to have their eyes forcibly kept open, which may involve the use of eye-drop anesthetic. In addition, it has become clear, with impatient subjects or subjects unfamiliar with the use of an input device, in particular, that the measurement results tend to indicate operating vision that is too low compared to the actual vision. More specifically, it has been known that, in many cases of actual measurement, the subjects inadvertently move a joystick even when they know the correct answers or the joystick does not operate properly as intended, thus leading to some errors. As a result, according to conventional measurements based on the premise that visual acuities decrease over time, measured operating vision tends to be lower than what they really are.

OBJECT AND SUMMARY OF THE INVENTION

Accordingly, it is an object of the present invention to provide a method and an apparatus that allow more accurate measurement of operating vision to be performed allowing natural blinking.

One aspect of the present invention provides a method for measuring operating vision. The method comprises: a displaying step of displaying an optotype mark on a display device; a response-accepting step of accepting, via an input device, a subject's response input in response to the displayed optotype mark; and a determining step of causing a computing device to determine whether the accepted response is correct or incorrect. If a result of the determination indicates that the current response of the subject is correct and a previous response or one of a previous and a last-but-one responses is incorrect, the computing device determines that an optotype mark corresponding to the same visual acuity as a current level of visual acuity is to be presented next. If the result indicates that the current response of the subject is correct and also indicates that the previous response is correct or both the previous and last-but-one responses are correct, the computing device determines that an optotype mark corresponding to visual acuity which is one level higher than a current level is to be presented. If the result indicates that the current response is incorrect, the computing device determines that an optotype mark corresponding to visual acuity which is one level lower than the current level is to be presented next. The method further comprises the steps of storing in a memory at least a visual acuity level corresponding to the displayed optotype mark and the result of the determination performed in the determining step; and determining whether a predetermined time or a predetermined number of display operations is reached. When the predetermined time or the predetermined number of display operations is not reached, the computing device causes an optotype mark corresponding to the result of the determination to be displayed in the display step. The method further comprises the step of causing an output device to output a measurement result when the predetermined time or a predetermined number of responses is reached.

The method of the present invention is executed by a system that includes a display device for displaying optotype marks in a manner in which a subject can easily see them, a computing device connected to the display device, an input device connected to the computing device, an output device, and a memory.

Alternatively, the computing device may determine that an optotype mark corresponding to visual acuity which is one level lower than the current level is to be presented next, if the result indicates that the current response is incorrect and if a previous response that directly precedes the current response is incorrect.

Another aspect of the present invention provides a method for analyzing operating vision. The analysis method comprises: a step of plotting, on a virtual graph indicating visual acuity values versus elapsed time, only visual acuity values for which correct answers were given; a step of determining, as an integral value A, a rectangular area on the virtual graph, the rectangular area being defined by a certain elapsed time of measurement and a visual acuity value corresponding to an optotype mark displayed at measurement start time; and a step of determining, as an integral value B, an area that lies between a polygonal line on the virtual graph and a reference straight line opposing the polygonal line and that lies between the measurement start time and the elapsed time, the polygonal line connecting only visual acuity values for which correct answers were given, the visual acuity values including the visual acuity value corresponding to the optotype mark displayed at the measurement start time. The analysis method further comprises: a step of determining a value resulting from dividing the integral value B by the integral value A; and a step of displaying the determined value resulting from the division. The analysis method can facilitate the analysis of measurement results of operating vision. The term "virtual graph" used herein refers to a graph utilized for computation. Although the virtual graph can be physically displayed, it does not need to be actually displayed to implement the analysis method. When the Y axis represents visual acuity and the X axis represents elapsed time, the opposing reference straight line may be the X axis or may be another appropriate straight line.

Preferably, the present invention further provides a program including instructions, executable by a computer, for implementing the method and a computer-readable storage medium in which such a program is stored.

Another aspect of the present invention provides an apparatus for measuring operating vision. The apparatus comprises a display device for displaying an optotype mark; an input device for accepting a subject's response input in response to the optotype mark displayed by the display device; and a controller for determining whether the accepted response is correct or incorrect. When a result of the determination indicates that the current response of the subject is correct and a previous response or one of a previous response and a last-but-one response is incorrect, the controller determines that an optotype mark corresponding to the same visual acuity is to be presented. When the result indicates that the current response of the subject is correct and also indicates that the previous response is correct or both the previous response and the last-but-one response are correct, the controller determines that an optotype mark corresponding to a visual acuity one level higher is to be presented. When the result indicates that the current response is incorrect, the controller determines that an optotype mark corresponding to a visual acuity one level lower is to be presented. The apparatus further comprises a memory for storing at least a visual acuity level corresponding to the displayed optotype mark and the result of the determination performed by the controller, and a timer for determining whether a predetermined time or a predetermined number of display operations is reached. When the predetermined time or the predetermined number of display operations is not reached, the controller causes the display device to display an optotype mark corresponding to the result of the determination. The apparatus further comprises an output device for outputting a measurement result when the predetermined time or a predetermined number of responses is reached.

Preferably, the operating vision measurement apparatus may include an infrared sensor or a camera so as to allow automatic measurement of the number of blinks. Since the temperature of the eyeball is generally lower than that of the eyelid, the blinking can be captured using an infrared sensor and recorded, making it possible to measure the number of blinks in a certain period of time. Alternatively, visual images captured by a camera are processed to capture the motion of the eyelid, thereby making it possible to determine the time and number of blinks.

Typically, the operating vision examination is performed at a distance of 5 m (which does not necessarily mean that the physical distance is 5 m, and it also includes a case in which the position at which the eye captures an image through an optical system is located at a distance of 5 m), while it may be performed at another distance. For example, the optical distance between the screen and the eye can also be set to about 30 to 50 cm. A result obtained by measurement with such a distance less than 5 m is called near vision. Operating vision for near vision (this operating vision is referred to as "operating near vision") can also be measured in the present invention. The operating near vision is considered to be significant in modern life in which many people engage in eye-straining desk and office work. In this case, the operating vision can be measured with the eye positioned at a predetermined distance of, for example, 30 cm, 50 cm, or 1 m, without the use of an optical system, i.e., directly, from a liquid crystal display or the like.

The term "optotype marks" used herein refers to various symbols used for measuring visual acuity. Examples of such marks include, preferably, Landolt C rings, E marks, numerals, and letters (e.g., optotypes used in Snellen charts, Roman alphabets or Japanese characters). For measurement of contrast visual acuity, which represents the ability to identify color densities, any symbols with color density variations can be used. In ordinary visual acuity examination, black symbols are displayed over white background. For contrast visual acuity measurements, grey symbols of different color densities are used and it is measured how visual acuity changes for different densities of grey symbols. For example, if the darkest black symbol has a contrast of 100%, it is tested if visual acuity is affected when a 25%, 50%, or 75% contrast (density of grey color) is used.

The term "computer-readable storage media" refers to storage media such as flash memories, hard disks, FDs (Floppy®) disks), CDs (compact discs), and MDs (mini discs), but is not limited thereto, as long as they are readable by computers.

In addition, in order to analyze obtained data, it is preferable to plot only visual acuity values for which correct answers were given, with the vertical axis for visual acuity and the horizontal axis for elapsed time. Assuming that the visual acuity does not degrade at all from the visual acuity corresponding to an optotype mark displayed at the time of starting a measurement, an integral value A of a rectangle on a graph is determined from the start time of the measurement to a certain elapsed time. Further, an area B indicated by a hatched portion below a polygonal line (shown in FIG. 6) from the start time to the elapsed time is determined, with the polygonal line connecting only visual acuity values for which correct answers have been given, the visual acuity values including the visual acuity value corresponding to the optotype mark displayed at the start time. The value of B/A is then determined and displayed as an integration result on operating vision. Subsequently, the value of B/A at each point of time at which a correct answer is given is determined. The determined value can be displayed as a ratio of operating vision to a first visual acuity value. This B/A value may be referred to as "vision maintenance value."

The results displayed can include at least one of (1) maximum and minimum visual acuities, (2) an average value, and (3) an integration result of operating visions (vision maintenance value), for each of normal operating vision and operating near vision. Needless to say, the results obtained at measurement points of time can be displayed in a tabular form. Displayed items may preferably be selected or changed as needed.

It is also possible to display the evolution of changes in visual acuity and the number of blinks. For example, when measurement is performed for 60 seconds while natural blinking is allowed, changes in visual acuity are displayed after each moment of blinking, with the moment being used as the origin point (0 second). Such an arrangement allows one to keep track of changes in visual acuity and see the overall variation in visual acuity after each blinking event. It is also possible to display time intervals between blinks, that is, a time from one blink to the next blink.

Still another aspect of the present invention provides an operating vision measurement method for a system that comprises a host computer and a subject's computer connected to the host computer through a communication network. The method comprises: a displaying step of causing the host computer to transmit an optotype mark to the subject's computer through the electrical communication line and displaying the optotype mark on a display of the subject's computer; a response-accepting step of causing the subject's computer to accept the subject's response input in response to the displayed optotype mark; a response-receiving step of causing the host computer to receive the response from the subject's computer through the electrical communication line; and a determining step of causing the host computer to determine whether the received response is correct or incorrect. When a result of the determination indicates that the current response of the subject is correct and a previous response or one of a previous response and a last-but-one response is incorrect, the host computer determines that an optotype mark corresponding to the same visual acuity is to be presented. When the result indicates that the current response of the subject is correct and also indicates that the previous response is correct or both the previous response and the last-but-one response are correct, the host computer determines that an optotype mark corresponding to a visual acuity one level higher is to be presented. When the result indicates that the current response is incorrect, the host computer determines that an optotype mark corresponding to a visual acuity one level lower is to be presented. The method further comprises: a storing step of causing a memory to store at least a visual acuity level corresponding to the displayed optotype mark and the result of the response correctness/incorrectness determination performed in the determining step; and a timer determining step of determining whether a predetermined time or a predetermined number of display operations is reached. When the predetermined time or the predetermined number of display operations is not reached, the computing device causes an optotype mark corresponding to the result of the response correctness/incorrectness determination to be displayed in the displaying step. The method further comprises a result displaying step of causing, when the predetermined time or a predetermined number of responses is reached, the host computer to compile measurement results and to transmit the measurement results to the subject's computer and causing the measurement results to be output on the display of the subject's computer.

Preferably, the subject's computer may be a mobile information terminal. The present invention further provides a computer-readable storage medium on which a program for implementing the measurement method is stored. The electronic communication may be implemented with any communication means used for transmitting and receiving electronic data. Examples include wireless links for mobile phones, phone lines, digital communication lines, analog telephone lines, and the TCP/IP-protocol-based Internet.

The operating vision measurement method or apparatus of the present invention allows operating vision to be measured with higher accuracy. The present invention allows a computer or a mobile information terminal to measure operating vision and/or contrast visual acuity. In the present invention, when an answer is incorrect or no response is given, an optotype mark corresponding to visual acuity which is one level lower than the current level is presented. When a correct answer is given once, an optotype mark corresponding to the same visual acuity is displayed, with the visual acuity level at this point being maintained. Further, when a correct response is consecutively given two or three times, an optotype mark corresponding to visual acuity which is one level higher than the current level is displayed based on the possibility that the actual visual acuity may be better, so as to check the actual visual acuity at this point. An optotype mark corresponding to a higher level of visual acuity is displayed when a correct answer is continuously given two or three times so as to deal with a careless error which may cause a measurement result of operating vision to indicate a lower value than the actual one. The reason why a single correct answer does not immediately lead to a raised level of visual-acuity by one step is to prevent undesirable variations in measured values from occurring due to a simple operational error of the subject.

DETAILED DESCRIPTION OF PREFERRED EMBODIMENTS

Embodiments according to the present invention will be described below with reference to the accompanying drawings.

First Embodiment

Operating Vision Measurement

Figure 1:
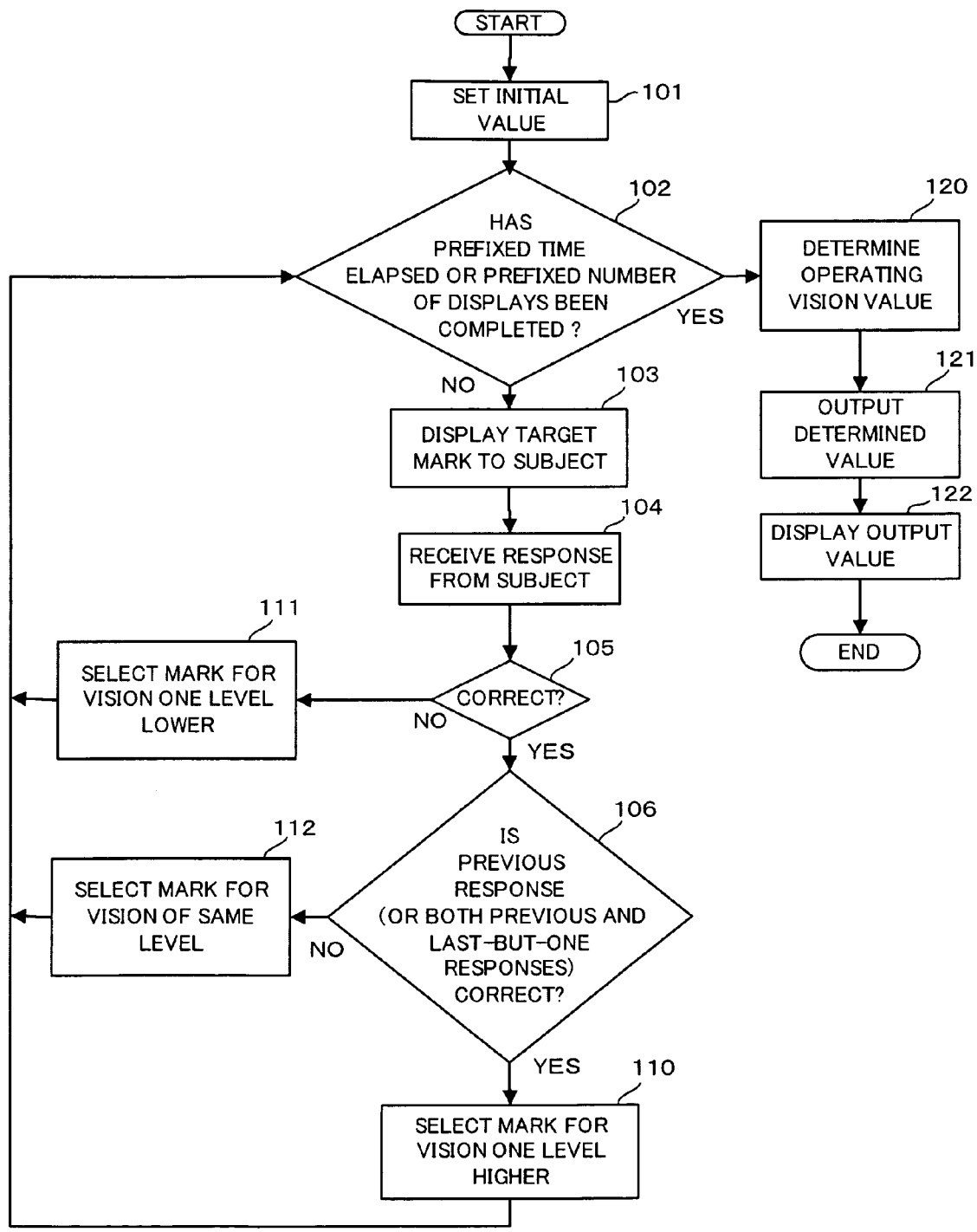
FIG. 1 is a flow chart showing the flow of processing in a first embodiment of the present invention.

FIG. 1 is a flow chart showing an operating vision measurement method according to a first embodiment of the present invention. The method of the present invention can be executed by a standalone or networked measurement apparatus that includes a display unit, inputting means, controlling means having computing means, a memory, and an output device.

First, in step 101, parameters related to the measurement of operating vision are set, as needed. Before starting to display optotype marks to a subject, a determination is made in step 102 as to whether or not a predetermined time has elapsed or a predetermined umber of displays has been completed. This determination step can be executed at any point in the method of the present invention. When the determination indicates NO, an optotype mark (e.g., a ring mark having a slit to indicate its opening direction) is displayed on the display unit in step 103. The optotype-mark display time, which is generally called the stimulus time, is essentially about 1 to 2 seconds but can be changed.

In step 104, the subject stares at the optotype mark and enters a response via the inputting means, such as a joystick. When numerals or letters (e.g., Roman alphabets or Japanese characters) are used for the optotype mark, the inputting means may be implemented with a microphone and voice recognition means to accept a voice response. The inputting means may also be implemented with other means, such as a mouse and/or a keyboard.

When the response from the subject is accepted in step 104, the controlling means determines whether the response is correct or incorrect and also determines an optotype mark to be displayed next. When an optotype mark having the same visual acuity level is to be displayed next, the next optotype mark can be randomly selected from multiple optotype marks corresponding to the visual acuity level. When the current response is correct in step 105, the controlling means refers to the previous response or both the previous response and the last-but-one response and makes a determination in step 106 as to whether or not the response(s) is correct. When the response(s) is correct in step 106, the controlling means determines in step 110 that an optotype mark corresponding to a visual acuity one level higher is to be displayed. When the previous response or one of the previous response and the last-but-one response is incorrect in step 106, the controlling means determines in step 112 that a randomly selected optotype mark corresponding to the same visual acuity is to be displayed. On the other hand, when the current response is incorrect in step 105, the controlling means determines in step 111 that an optotype mark corresponding to a visual acuity one level lower is to be displayed. In this case, when no input is received during the aforementioned stimulus time or within a predetermined time subsequent thereto, it is determined that the corresponding response is incorrect.

Thus, a stimulus time of, for example, 2 to 3 seconds (or a time during which one optotype mark is continuously displayed) is set and measurement is continuously performed until a time set by a timer function is reached or a predetermined number of display operations is reached. The controlling means computes, for example, a measurement value indicating the lowest visual acuity of the measurement results and outputs the computed measurement value to result-displaying means. After the processing described below is performed, necessary or preferable data is eventually displayed. The display of optotype marks is repeated during the set time of the timer function. The displaying may be performed at regular intervals, as described above, or may be performed when a response from the joystick is received. In the latter case, for a subject who is quick in giving responses, the optotype marks can be displayed at intervals of 1 second or less, so that accurate results can be obtained.

First Experimental Example

Figure 5:
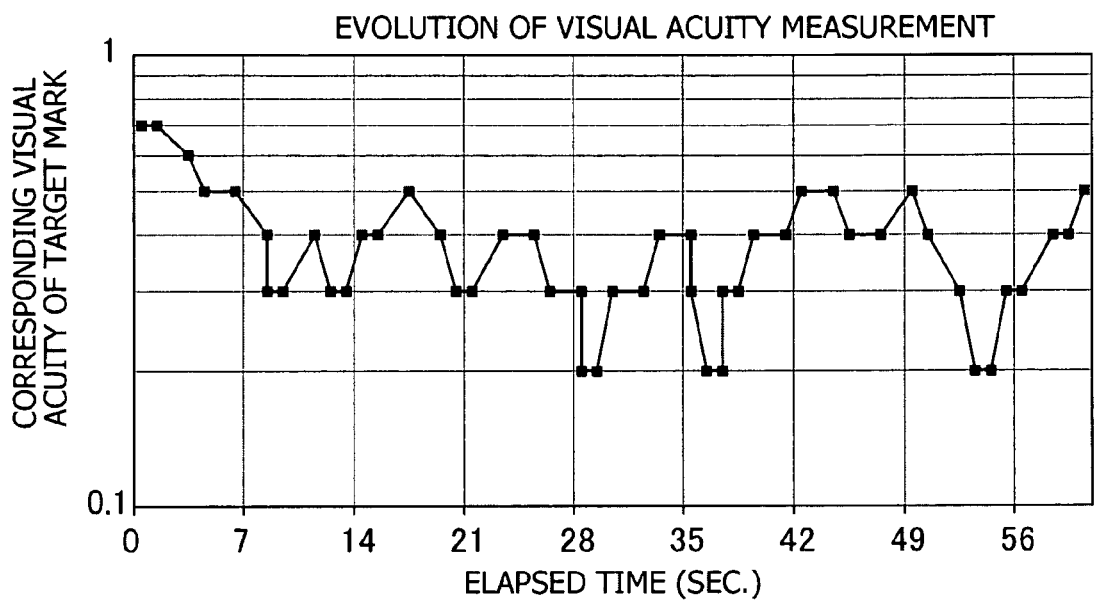
FIG. 5 is a graph showing an example of results obtained in the first embodiment of the present invention.

Table 1 shows one example of operating vision measurement results obtained as described above. In this table, results for corresponding responses are shown in respective rows. The contrast was set to 100%. The stimulus time was set to 2 seconds. Elapse of the stimulus time was also regarded as being equivalent to the absence of a response, and such a case was processed in the same manner an incorrect response. An optical system of the measurement apparatus was set to have an examination distance of 5 meters. When two consecutive correct answers were received at the same visual acuity level, the visual acuity was increased by one level to display a smaller optotype mark. The elapsed time represents, in seconds, the time from starting measurement until a corresponding response is received. The second column shows corresponding visual acuities (decimal visual acuities) of optotype marks presented with respect to responses and common logarithms (LogMAR: Logarithm of Minimum Angle of Resolution) expressed by the reciprocals of the fractional visual acuities. The reason for taking the logarithms is that the results are easy to see when shown in the form of a graph. In addition, integral values can also be included in this table so as to correspond to the respective visual acuities. The result attribute "o" indicates a correct answer and the result attribute "x" indicates an incorrect answer. Each blank field indicates that no response was given. As can be seen from the table, the first correct answer was given for a visual acuity of 0.5 and the minimum visual acuity was 0.2. In this experimental example, the number of blinks, which was counted by visual observation, was 10. FIG. 5 is a graph showing the evolution of this visual acuity measurement. The X axis represents elapsed time when a response was given and the Y axis represents a visual acuity value corresponding to an optotype mark displayed when a response was given. Since the graph does not indicate whether or not the subject's responses were correct, reading an operating vision from the graph should be done with care; nevertheless, the graph reveals a general trend of the measurement results. Also, when blinking events are monitored, each occurrence of blinking may be show in an additional column provided in Table 1 using a suitable symbol. Such blinking event may be shown in FIG. 5 using such symbol as a small arrow. The display of blinking events in a table or a graph makes it easy to analyze or understand measurement results of operating visual acuity in a more intuitive manner.

Table 2 shows results when operating vision was determined using a known technique, for the same subject under the same conditions, except that the visual acuity level for an optotype mark to be displayed was not increased regardless of how many times correct answers were continuously given at the same visual acuity level. Although the measurement time was 60 seconds, Table 2 shows only results up to an elapsed time of 39.13 seconds. This measurement did not involve forcible eye opening and was thus performed during natural blinking. The number of blinks, which was counted by visual observation, was 13 in 60 seconds. Except for the initial response, the maximum visual acuity was 0.5 and the minimum visual acuity was 0.2.

TABLE 1

| Elapsed Time (sec.) | Visual Acuity/ Logarithm | Result Attribute | Response Interval (sec.) |
| --- | --- | --- | --- |
| 1.03 | 0.7/+0.15 | No | 1.03 |
| 3.03 | 0.6/+0.22 | | 2.00 |
| 4.06 | 0.5/+0.3 | Yes | 1.03 |
| 6.06 | 0.5/+0.3 | | 2.00 |
| 8.06 | 0.4/+0.4 | | 2.00 |
| 8.91 | 0.3/+0.52 | Yes | 0.84 |
| 9.88 | 0.3/+0.52 | Yes | 0.97 |
| 11.88 | 0.4/+0.4 | | 2.00 |
| 12.86 | 0.3/+0.52 | Yes | 0.98 |
| 13.84 | 0.3/+0.52 | Yes | 0.99 |
| 14.97 | 0.4/+0.4 | Yes | 1.13 |

TABLE 1-continued

| Elapsed Time (sec.) | Visual Acuity/ Logarithm | Result Attribute | Response Interval (sec.) |
|---|---|---|---|
| 15.86 | 0.4/+0.4 | Yes | 0.89 |
| 17.86 | 0.5/+0.3 | | 2.00 |
| 19.86 | 0.4/+0.4 | | 2.00 |
| 20.8 | 0.3/+0.52 | Yes | 0.94 |
| 21.78 | 0.3/+0.52 | Yes | 0.98 |
| 23.13 | 0.4/+0.4 | Yes | 1.34 |
| 25.13 | 0.4/+0.4 | | 2.00 |
| 26.03 | 0.3/+0.52 | Yes | 0.91 |
| 28.03 | 0.3/+0.52 | | 2.00 |
| 28.73 | 0.2/+0.7 | Yes | 0.70 |
| 29.52 | 0.2/+0.7 | Yes | 0.78 |
| 30.45 | 0.3/+0.52 | Yes | 0.94 |
| 32.05 | 0.3/+0.52 | Yes | 1.59 |
| 33.33 | 0.4/+0.4 | Yes | 1.28 |
| 35.33 | 0.4/+0.4 | | 2.00 |
| 35.41 | 0.3/+0.52 | No | 0.08 |
| 36.22 | 0.2/+0.7 | Yes | 0.81 |
| 37.05 | 0.2/+0.7 | Yes | 0.83 |
| 37.94 | 0.3/+0.52 | Yes | 0.89 |
| 38.86 | 0.3/+0.52 | Yes | 0.92 |
| 39.97 | 0.4/+0.4 | Yes | 1.11 |
| 41.72 | 0.4/+0.4 | Yes | 1.75 |
| 42.69 | 0.5/+0.3 | Yes | 0.97 |
| 44.69 | 0.5/+0.3 | | 2.00 |
| 45.98 | 0.4/+0.4 | Yes | 1.30 |
| 47.36 | 0.4/+0.4 | Yes | 1.38 |
| 49.36 | 0.5/+0.3 | | 2.00 |
| 50.45 | 0.4/+0.4 | No | 1.09 |
| 52.45 | 0.3/+0.52 | | 2.00 |
| 53.39 | 0.2/+0.7 | Yes | 0.94 |
| 54.22 | 0.2/+0.7 | Yes | 0.83 |
| 55.36 | 0.3/+0.52 | Yes | 1.14 |
| 56.38 | 0.3/+0.52 | Yes | 1.02 |
| 58.33 | 0.4/+0.4 | Yes | 1.95 |
| 59.73 | 0.4/+0.4 | Yes | 1.14 |
| 60 | 0.5/+0.3 | | E |

TABLE 2

| Elapsed Time (sec.) | Visual Acuity/ Logarithm | Result Attribute | Response Interval (sec.) |
|---|---|---|---|
| 1.70 | 0.7/+0.15 | Yes | 0.70 |
| 2.42 | 0.7/+0.15 | No | 0.72 |
| 2.53 | 0.6/+0.22 | No | 0.11 |
| 3.25 | 0.5/+0.3 | Yes | 0.72 |
| 3.92 | 0.5/+0.3 | Yes | 0.67 |
| 4.81 | 0.5/+0.3 | Yes | 0.89 |
| 5.77 | 0.57/+0.3 | Yes | 0.95 |
| 6.50 | 0.5/+0.3 | Yes | 0.73 |
| 7.86 | 0.5/+0.3 | Yes | 1.36 |
| 9.86 | 0.5/+0.3 | | 2.00 |
| 10.47 | 0.4/+0.4 | No | 0.61 |
| 12.47 | 0.3/+0.52 | | 2.00 |
| 13.19 | 0.2/+0.7 | Yes | 0.72 |
| 13.67 | 0.2/+0.7 | Yes | 0.48 |
| 14.30 | 0.2/+0.7 | Yes | 0.63 |
| 14.80 | 0.2/+0.7 | Yes | 0.50 |
| 15.34 | 0.2/+0.7 | Yes | 0.55 |
| 16.06 | 0.2/+0.7 | Yes | 0.72 |
| 16.59 | 0.2/+0.7 | Yes | 0.53 |
| 17.17 | 0.2/+0.7 | Yes | 0.58 |
| 17.70 | 0.2/+0.7 | Yes | 0.53 |
| 18.25 | 0.2/+0.1 | Yes | 0.55 |
| 19.05 | 0.2/+0.7 | Yes | 0.80 |
| 19.66 | 0.2/+0.7 | Yes | 0.61 |
| 20.41 | 0.2/+0.7 | Yes | 0.75 |
| 21.19 | 0.2/+0.7 | Yes | 0.78 |
| 21.91 | 0.2/+0.7 | Yes | 0.72 |
| 22.49 | 0.2/+0.7 | Yes | 0.58 |
| 23.22 | 0.2/+0.7 | Yes | 0.73 |
| 24.11 | 0.2/+0.7 | Yes | 0.89 |
| 24.77 | 0.2/+0.7 | Yes | 0.66 |

TABLE 2-continued

| Elapsed Time (sec.) | Visual Acuity/ Logarithm | Result Attribute | Response Interval (sec.) |
|---|---|---|---|
| 25.75 | 0.2/+0.7 | Yes | 0.98 |
| 26.38 | 0.2/+0.7 | Yes | 0.63 |
| 27.02 | 0.2/+0.7 | Yes | 0.64 |
| 27.84 | 0.2/+0.7 | Yes | 0.63 |
| 28.47 | 0.2/+0.7 | Yes | 0.83 |
| 29.08 | 0.2/+0.7 | Yes | 0.61 |
| 29.80 | 0.2/+0.7 | Yes | 0.72 |
| 30.63 | 0.2/+0.7 | Yes | 0.83 |
| 31.25 | 0.2/+0.7 | Yes | 0.63 |
| 32.20 | 0.2/+0.7 | Yes | 0.95 |
| 33.03 | 0.2/+0.7 | Yes | 0.83 |
| 33.61 | 0.2/+0.7 | Yes | 0.58 |
| 34.38 | 0.2/+0.7 | Yes | 0.77 |
| 34.99 | 0.2/+0.7 | Yes | 0.61 |
| 35.59 | 0.2/+0.7 | Yes | 0.61 |

Figure 6:
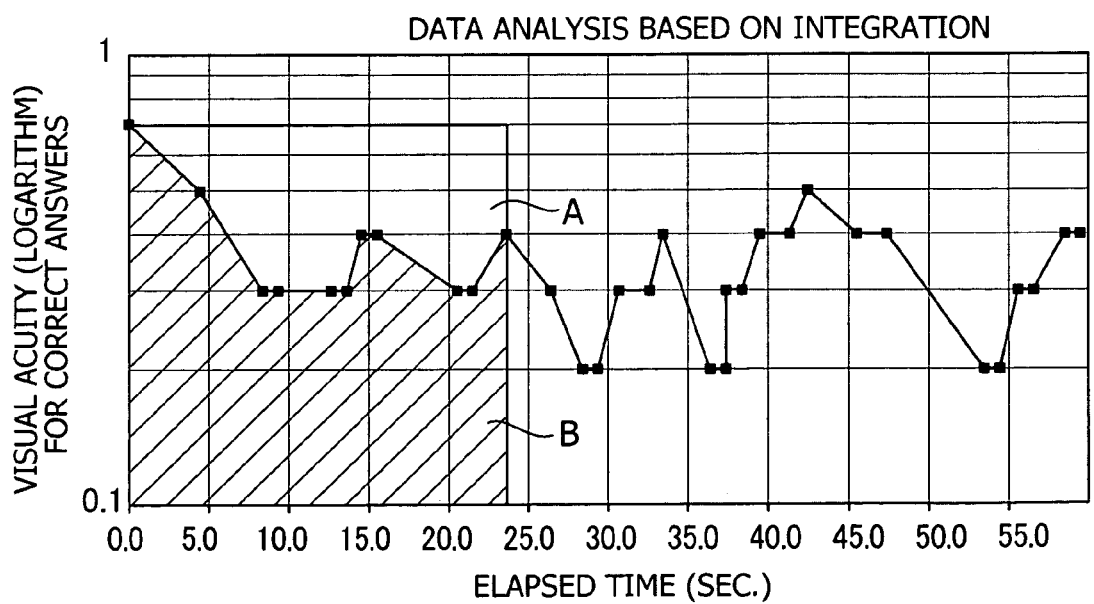
FIG. 6 is a graph showing an analysis method using integral values in connection with the first embodiment of the present invention.

In addition, FIG. 6 illustrates a method for analyzing the resulting data. In FIG. 6, only visual acuity values for which correct answers were given are plotted, with the vertical axis representing the logarithms of decimal visual acuities and the horizontal axis representing elapsed time. An integral value on the graph from the visual acuity (a decimal visual acuity of 0.7) at the start of measurement to a certain plotted point is determined assuming that the visual acuity does not decrease. The integral value represents an area denoted by A (which includes not only the white area but also the area lying between the bottom of the white area and the X axis). Area B indicated by the hatched portion below a polygonal line that connects only visual acuity values for which correct answers were given, including the measurement start time, is determined and B/A is then determined. The resulting value can be displayed as an integration result of operating vision. Subsequently, the values of B/A at respective points at which correct answers were given are determined. The determined values can be displayed as average operating vision. Displaying those values makes it easier to evaluate the data and makes it possible to compare visual acuities obtained in the conventional visual acuity examination with the operating vision. That is, this method makes it possible to know to what percentage of visual acuity at measurement start time or visual acuity in the conventional visual acuity examination each operating vision corresponds, and also makes it possible determine to what extent visual acuity over time or the visual function in everyday life (i.e., operating vision) represents visual acuity obtained in the conventional acuity examination. Table 3 shows an example of the values of B/A obtained as described above.

TABLE 3

| Elapsed Time (sec.) | Visual Acuity/ Logarithm | Result Attribute | B/A | Response Interval (sec.) |
|---|---|---|---|---|
| 1.00 | 0.4/+0.4 | | | 1.00 |
| 1.14 | 0.3/+0.52 | No | | 0.14 |
| 1.64 | 0.2/+0.7 | Yes | 0.9 | 0.50 |
| 2.11 | 0.2/+0.7 | Yes | 0.88 | 0.47 |
| 2.59 | 0.3/+0.52 | Yes | 0.9 | 0.49 |
| 3.03 | 0.3/+0.52 | Yes | 0.9 | 0.44 |
| 3.53 | 0.4/+0.4 | Yes | 0.92 | 0.50 |
| 4.02 | 0.4/+0.4 | Yes | 0.93 | 0.48 |
| 4.53 | 0.4/+0.4 | Yes | 0.94 | 0.52 |
| 5.06 | 0.4/+0.4 | Yes | 0.94 | 0.53 |
| 5.47 | 0.4/+0.4 | Yes | 0.95 | 0.41 |
| 5.97 | 0.4/+0.4 | Yes | 0.95 | 0.50 |
| 6.86 | 0.4/+0.4 | No | | 0.89 |
| 7.25 | 0.3/+0.52 | No | | 0.39 |

TABLE 3-continued

| Elapsed Time (sec.) | Visual Acuity/ Logarithm | Result Attribute | B/A | Response Interval (sec.) |
|---|---|---|---|---|
| 7.61 | 0.2/+0.7 | Yes | 0.94 | 0.36 |
| 7.94 | 0.2/+0.7 | No | | 0.33 |
| 8.27 | 0.1/+1.0 | No | | 0.33 |
| 8.59 | 0.09/+1.05 | Yes | 0.91 | 0.33 |
| 8.97 | 0.09/+1.05 | No | | 0.38 |
| 9.48 | 0.08/+1.1 | Yes | 0.88 | 0.52 |
| 9.78 | 0.08/+1.1 | Yes | 0.87 | 0.30 |
| 10.34 | 0.09/+1.05 | Yes | 0.86 | 0.56 |
| 10.86 | 0.09/+1.05 | Yes | 0.84 | 0.52 |
| 11.39 | 0.1/+1.0 | Yes | 0.83 | 0.53 |
| 11.83 | 0.1/+1.0 | No | | 0.44 |
| 12.22 | 0.09/+1.05 | No | | 0.39 |
| 12.55 | 0.08/+1.1 | No | | 0.33 |
| 12.92 | 0.07/+1.15 | No | | 0.38 |
| 13.23 | 0.06/+1.22 | No | | 0.31 |
| 13.80 | 0.05/+1.30 | Yes | 0.78 | 0.56 |
| 14.28 | 0.05/+1.30 | Yes | 0.77 | 0.48 |
| 14.70 | 0.06/+1.22 | Yes | 0.76 | 0.42 |
| 15.00 | 0.06/+1.22 | E | 0.76 | |

The measurement results shown in Table 3 were obtained under the following conditions: an examination distance of 1.0 meter, a contrast of 100%, and a stimulus time of 1 second. With an examination distance of 1 meter, unlike a commonly used examination distance of 5 m, the apparatus used in this embodiment can measure only a visual acuity of 0.4 to 0.01. Thus, the maximum visual acuity was 0.4. This maximum visual acuity continued seven times from 3.53 seconds to 6.86 seconds. The measured visual acuity greatly varies in the range of 0.4 to 0.05, whereas the values of B/A remain relatively stable, which facilitates quick understanding and assessment of what the measurement results indicate.

Operating vision data displayed by the known operating vision measurement is the last visual acuity obtained within the measurement time. However, according to the present invention, the integral values described above are determined and, when measurement is performed with settings for coping with variations in visual acuity, rather than the last visual acuity, the value of B/A, which is eventually obtained, or the ratio of a operating vision value to a first visual acuity value, can be displayed for assessment of the operating vision. These results are effective and significant compared to a case in which a final visual acuity is merely displayed.

It is preferable that the display of the table, the display of the integral values and the average operating vision value, and the display of the graph be switchable by a single-touch operation. It is also preferable that the measurement of operating near vision, the measurement of a normal operating vision, and the display thereof be switchable by a single-touch operation.

Second Embodiment

Operating Vision Measurement Apparatus

Figure 2:
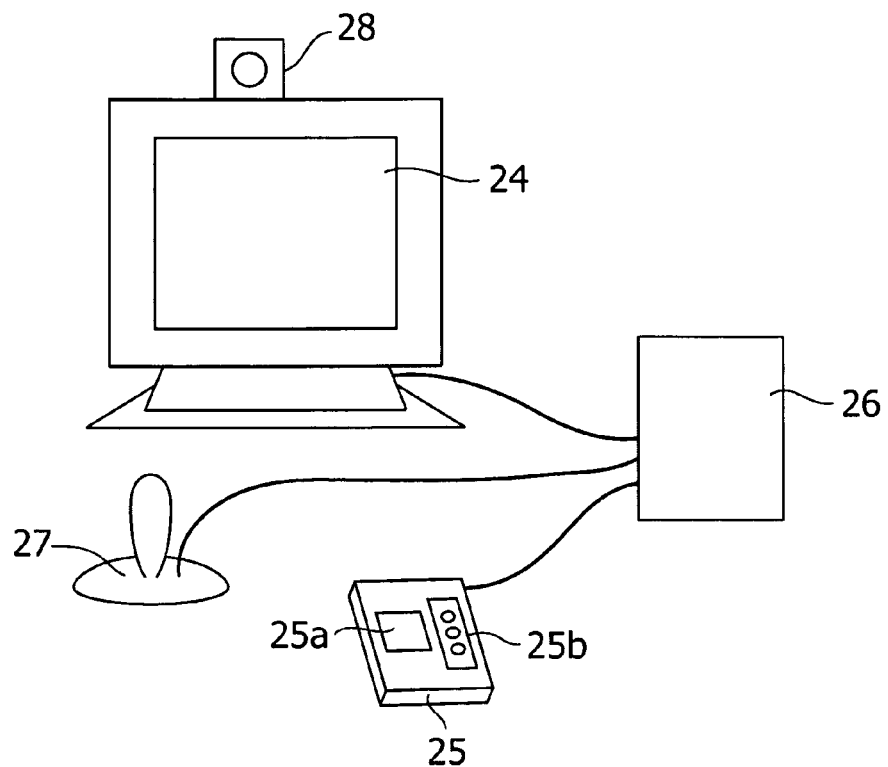
FIG. 2 is a schematic diagram showing the configuration of a second embodiment of the present invention.

FIG. 2 is a schematic diagram of an operating vision measurement apparatus according to another embodiment of the present invention. The operating vision measurement apparatus includes a display device 24; a timer function 25 for configuring and starting the operation, controlling means 26 including a computing device; a joystick 27; and image-capturing means 28 (e.g., an infrared sensor or camera) for capturing blinks. The timer function 25 is provided with a measurement start button 25a and setting means 25b.

A measurement procedure in this embodiment will be described next. The system of this embodiment has a standalone configuration and thus is not connected to a network. A power switch (not shown) is turned on and a subject faces the screen of the display device 24 at a predetermined distance therefrom. The distance in this case refers to a distance of, for example, 50 cm, for near visual acuity measurement. For example, a button included in the setting means 25b of the timer function 25 is pressed to set the measurement time to a predetermined value, e.g., 60 seconds, and the measurement start button 25a is then pressed. In response, visual acuity measurement is started. The image-capturing means 28 is provided above the screen of the display device 24 to monitor the number of blinks of the subject.

The subject stares at optotype marks (e.g., ring marks each having a slit to indicate its opening direction) displayed on the screen of the display device 24 one after another and gives responses with the joystick 27. When numerals or letters are used as the optotype marks, a microphone and voice recognition means can be used as inputting means to accept a voice response. The optotype-mark display time, which is generally called the stimulus time, is essentially about 1 to 2 seconds but can be changed. The controlling means 26 determines whether each response is correct or incorrect and determines an optotype mark to be displayed next. When an optotype mark having the same visual acuity level is to be displayed next, the next optotype mark can be randomly selected from multiple optotype marks corresponding to the visual acuity level.

That is, when the current response is correct, the controlling means 26 refers to the previous response or both the previous response and the last-but-one response and determines whether or not the response(s) is correct. When the response(s) is correct, the controlling means 206 determines that an optotype mark corresponding to a visual acuity one level higher is to be displayed. When the previous response or one of the previous response and the last-but-one response is incorrect, the controlling means determines that a randomly selected optotype mark corresponding to the same visual acuity is to be displayed. On the other hand, when the current response is incorrect, the controlling means 26 determines that an optotype mark corresponding to a visual acuity one level lower is to be displayed. In this case, when no input is received during the aforementioned stimulus time or within a predetermined time subsequent thereto, it is determined that the corresponding response is incorrect.

Thus, during measurement, when no response is received during a stimulus time of, for example, 2 seconds, the optotype marks displayed are switched at intervals of 2 seconds, and when a response is received before the end of the stimulus time, the optotype marks displayed are switched upon reception of the response. The measurement is continuously performed until a set time of the timer function 25 is exceeded or a preset number of display operations is reached. The controlling means 26 outputs, for example, the measurement results on the screen of the display device 24. The display of the optotype marks is repeated during the set time of the timer function 25. This display switching may be performed at regular intervals, as described above, or may be performed when a response from the joystick 27 is received. In the latter case, for a subject who is quick in giving responses, more optotype marks can be displayed and more responses can be detected, so that more accurate results can be obtained.

Third Embodiment

Operating Vision Measurement Apparatus

Figure 3:
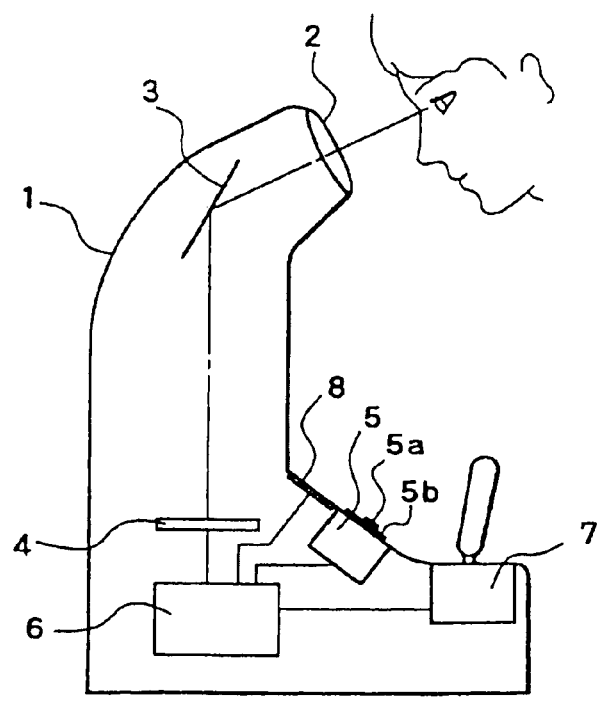
FIG. 3 is a schematic diagram showing the configuration of a third embodiment of the present invention.

FIG. 3 is a schematic diagram of one example of an operating vision measurement apparatus. An eyepiece 2, a mirror 3, and an optotype-mark display unit 4 are disposed in a housing 1 so that a subject can view an optotype mark, reflected by the mirror 3 and displayed on the optotype-mark display unit 4, through the eyepiece 2. As shown in FIG. 3, a timer function 5, controlling means 6, a joystick 7, and displaying means 8 (e.g., a liquid crystal display device) are disposed inside the housing 1 and on a surface thereof. The joystick 7 serves as inputting means for accepting the subject's response with respect to an optotype-mark displayed by the optotype-mark display unit 4. The controlling means 6 controls the displaying of the optotype-mark display unit 4 and determines whether the subject's response accepted via the inputting means is correct or incorrect. The timer function 5 is used to determine whether a preset time or a preset number of display operations is reached during measurement. The displaying means 8 outputs measurement results. The controlling means 6 generally includes computing means, a memory, and software that runs on the computing means and uses the memory. The controlling means 6 is connected to the optotype-mark display unit 4, the joystick 7, the timer function 5, and the displaying means 8 to control the optotype-mark display unit 4, to determine whether a response is correct or incorrect, to maintain a measurement mode by using the timer function 5, and to compute measurement results. The timer function 5 is provided with a measurement start button 5a, around which is provided a setting dial 5b for changing the number of set responses or the set time of the timer function 5.

Fourth Embodiment

Operating Vision Measurement Using a Computer or Mobile Terminal

Figure 4:
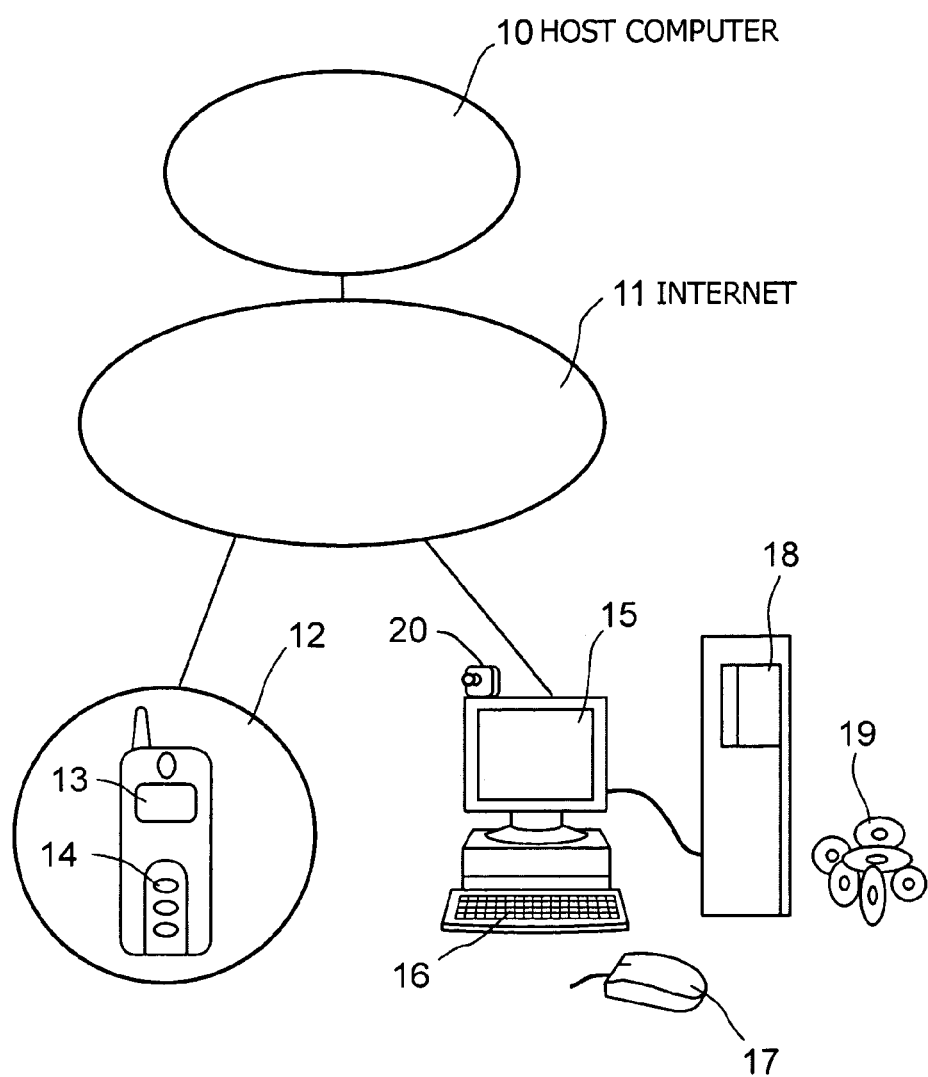
FIG. 4 is a schematic diagram showing the configuration of a system used for implementing a method in the fourth embodiment of the present invention.

FIG. 4 is a schematic diagram showing an operating vision measurement system using a computer or a mobile information terminal according to still another embodiment of the present invention. A display 15 of a computer 18 or a display 13 of a mobile information terminal 12, the displays 15 and 13 serving as displaying means, displays optotype marks. Examples of the optotype marks include Landolt rings, E marks, or letters (e.g., alphabets or characters of any languages). A mouse 17, a keyboard 16, and an input section 14 of the mobile information terminal 12 are used as response-accepting means with which a subject enters a response indicating the recognition of each optotype mark. A software program, which serves as determining means for determining whether a response is correct or incorrect, resides on a host computer 10, which is connected through an Internet 11. A timer function for putting the displaying means and the response-accepting means into a measurement mode during a set measurement time can be realized by a software program that runs on the host computer 10 connected through the Internet 11. The display 15 of the computer 18 or the display 13 of the mobile information terminal 12 is used as result-displaying means for displaying measurement results.

Figure 7:
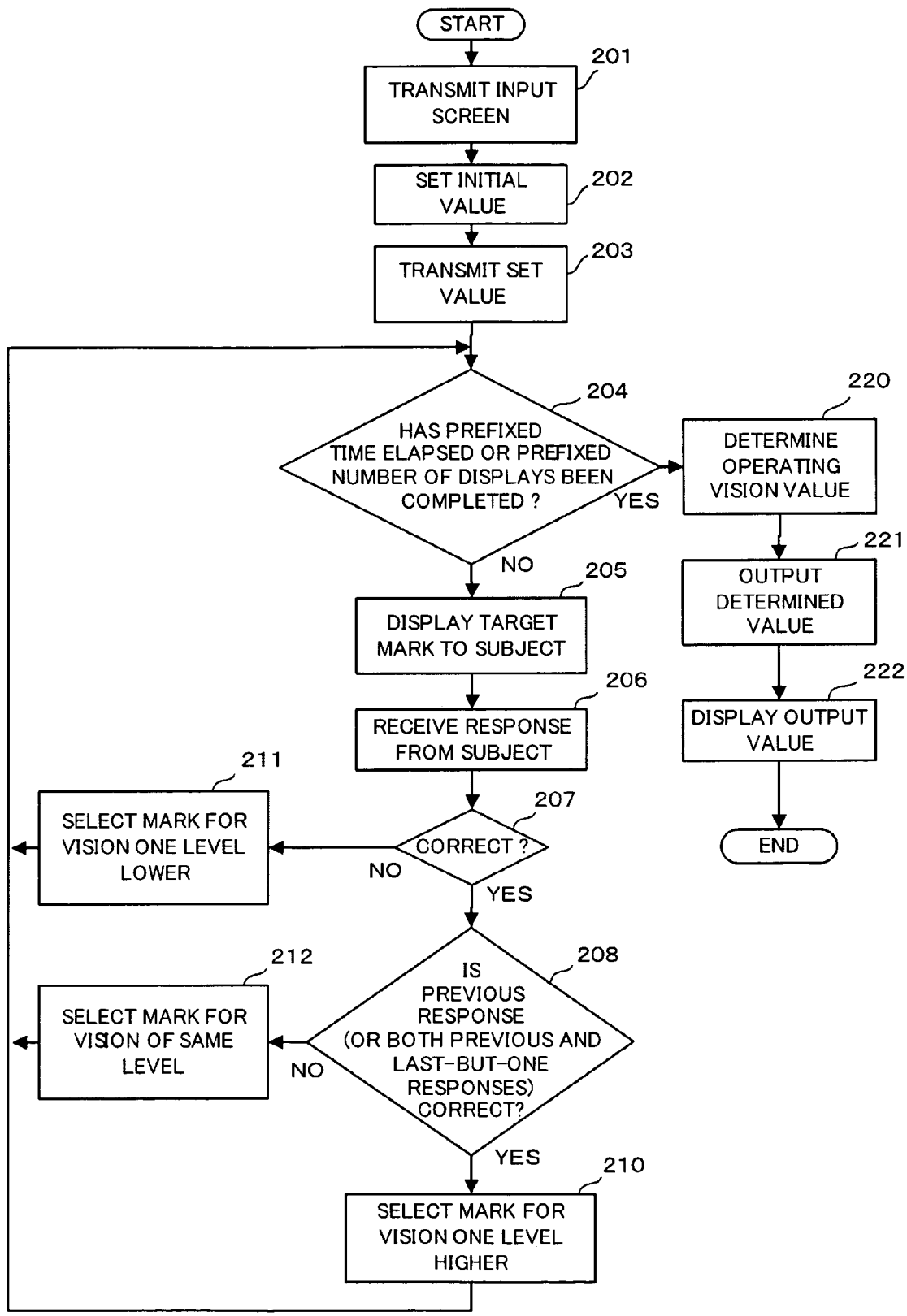
FIG. 7 is a flow chart showing the flow of processing in a fourth embodiment of the present invention.

A measurement method using the system of the fourth embodiment will now be described with reference to the flow chart shown in FIG. 7. The subject establishes a connection from the computer 18 or the mobile information terminal 12 to a specific website according to an internet protocol connection system. In step 201, the subject issues a request for source data in an HTML format or the like to the host computer 10 responsible for the specific website, so that an initial-measurement input screen for operating vision measurement is transmitted to the computer 18 or the mobile information terminal 12. In step 202, using the screen for input, the subject enters input values for measurement. Examples of the input values include the size of the subject's display screen, the distance between the subject's eyes and the display screen, and a set time of the timer function (i.e., measurement time). In this case, numeric values may be input using the keyboard or by selecting values from a table. Those input values can also be fixed. In step 203, the input values are transmitted to the host computer 10 and are stored thereon. Next, the subject clicks a measurement start button. In response, in step 205, the displaying of an optotype mark on the subject's display 13 or 15 is initiated and visual acuity measurement is started. In this case, a determination is made in step 204 as to whether or not a predetermined measurement time has elapsed.

The subject stares at the optotype mark displayed on the display 13 or 15 and enters a response via the mobile-information-terminal input section 14 or the keyboard 16 and/or the mouse 17. The response is then transmitted to the host computer 10 through the Internet 11. The determining means on the host computer 10 determines whether the response is correct or incorrect and determines an instruction for an optotype mark to be displayed next on the display 13 or 15. The determination of an optotype mark to be displayed is made as in the first embodiment. When a predetermined time has elapsed or a predetermined number of display operations has been reached in step 204, for example, measurement results of those response data are compiled and visual-acuity measurement values indicating the lowest visual acuity of the measurement results are compiled. The visual-acuity measurement results are displayed on the display 13 or 15, which serves as result-displaying means. On the other hand, when it is determined in step 204 that a predetermined time has elapsed or a predetermined number of display operations has been reached, in steps 220 to 222, a measurement result indicating the minimum visual acuity is selected from measurement results obtained during the last half of the set time, excluding some initial measurement results, and is then displayed on the display 13 or 15 as a operating vision value. The result indicates the operating vision of the subject. The display of optotype marks is repeated during the set time of the timer function. The display operation may be performed at regular intervals, as described above, or may be performed when a response is received by the response-accepting means. In the latter case, for a subject who is quick in giving responses, optotype marks can be displayed at intervals of 2 seconds or less, so that more accurate results can be obtained.

Fifth Embodiment

Contrast Visual Acuity Measurement Method Using a Computer or Mobile Terminal A description will now be given of a contrast visual-acuity measurement system using a computer or mobile information terminal according to yet another embodiment of the present invention. This contrast visual-acuity measurement method is analogous in system configuration and measurement scheme to the operating vision measurement method of the first embodiment, except that the optotype marks are changed to those suitable for contrast measurement. The optotype marks for contrast visual-acuity measurement may be implemented with marks having variations in brightness.

Other Embodiments

Although not shown, other embodiments according to the present invention will be described next. Presenting means for presenting optotype marks may be configured with a large screen and a projector. In this case, the projector is connected to the controlling means to project the optotype marks onto the screen. A subject stares at the optotype marks and gives responses via response-accepting means, such as a joystick or keyboard. The optotype marks displayed on the display may be not only marks representing conventional Landolt rings, E marks, letters (e.g., optotypes used in Snellen charts or characters of Japanese or any other languages), or the like, but also any kind of marks indicating directions, such as up, down, left, and right. Examples include marks representing animation characters or traffic signs. The present invention is also applicable to a dynamic visual-acuity examination using, for example, a car driving game in which a subject plays the role of a driver and traffic signs appear ahead along a road. The response-accepting means is not limited to the input section of the mobile information terminal or the keyboard and mouse connected to the computer; it may also be implemented with a joystick or an optical communication input device, such as a cordless mouse, for giving responses. Such embodiments are applicable to operating vision measurement that can be performed while the subject feels like he or she is playing a game and also to education for operating vision measurement.

A software program responsible for the control and the set-time timer function can not only be made available on a web site connected through the Internet, but may also be stored on computer-readable storage media, such as CD-ROMs and DVDs, for distribution as promotional products of eye clinics, eyeglasses shops, and so on. The system may have functions that allow periodically-measured results to be recorded on a web site or a user storage medium, such as a hard disk, and that allow a time-series chart of the measurement results to be displayed and/or printed. Data may be processed so that the time-series chart can be used during questioning by ophthalmologists.

What is claimed is:

1. A method for measuring operating visual acuity, comprising:
    a displaying step of displaying an optotype mark on a display device;
    a response-accepting step of accepting, via an input device, a subject's response input in response to the displayed optotype mark;
    a determining step of causing a computing device to determine whether the accepted response is correct or incorrect, wherein
        if a result of the determination indicates that the current response of the subject is correct and if a previous response or one of a previous and a last-but-one responses is incorrect, the computing device determines that an optotype mark corresponding to the same visual acuity as a current visual acuity is to be presented next;
        if the result indicates that the current response of the subject is correct and if the previous response is correct or both the previous and last-but-one responses are correct, the computing device determines that an optotype mark corresponding to visual acuity which is one level higher than a current level is to be presented next; and
        if the result indicates that the current response is incorrect, the computing device determines that an optotype mark corresponding to visual acuity which is one level lower than the current level is to be presented next;
    a storing step of storing in a memory at least a visual acuity level corresponding to the displayed optotype mark and the result of determination performed in the determining step;
    a timer-determining step of determining whether a predetermined time or a predetermined number of display operations is reached, wherein if the predetermined time or the predetermined number of display operations is not reached, the computing device causes an optotype mark corresponding to the result of the determination to be displayed next in a subsequent displaying step; and
    an output step of causing an output device to output a measurement result when the predetermined time or a predetermined number of responses is reached.

2. The method according to claim 1, wherein the computing device determines that an optotype mark corresponding to visual acuity which is one level lower than the current level is to be presented next, not only if the result indicates that the current response is incorrect, but also if a previous response that directly precedes the current response is incorrect.

3. An apparatus for measuring operating vision, comprising:
    a display device for displaying an optotype mark;
    an input device for accepting a subject's response input in response to the optotype mark displayed on the display device;
    a controller for determining whether the accepted response is correct or incorrect, wherein
        if a result of the determination indicates that the current response of the subject is correct and if a previous response or one of a previous and a last-but-one responses is incorrect, the controlling means determines that an optotype mark corresponding to the same visual acuity level as a current level is to be presented next;
        if the result indicates that the current response of the subject is correct and if the previous response is correct or both the previous and last-but-one responses are correct, the controlling means determines that an optotype mark corresponding to visual acuity which is one level higher than a current level is to be presented next; and
        if the result indicates that the current response is incorrect, the controlling means determines that an optotype mark corresponding to visual acuity which is one level lower than the current level is to be presented next;
    a memory for storing at least a visual acuity level corresponding to the displayed optotype mark and the result of the determination performed by the controlling means;
    a timer for determining whether a predetermined time or a predetermined number of display operations is reached, wherein when the predetermined time or the predetermined number of display operations is not reached, the controlling means causes the display device to display an optotype mark corresponding to the result of the determination, and an output device for outputting a measurement result when the predetermined time or predetermined number of responses is reached.

4. An operating vision measurement method for a system that comprises a host computer and a subject's computer connected to the host computer, comprising:

a displaying step of causing the host computer to transmit an optotype mark to the subject's computer through the electrical communication line and displaying the optotype mark on a display of the subject's computer;

a response-accepting step of causing the subject's computer to accept the subject's response input in response to the displayed optotype mark;

a response-receiving step of causing the host computer to receive the response from the subject's computer through the electrical communication line;

a determining step of causing the host computer to determine whether the received response is correct or incorrect, wherein if a result of the determination indicates that the current response of the subject is correct and if a previous response or one of a previous and a last-but-one responses is incorrect, the host computer determines that an optotype mark corresponding to the level of the same visual acuity as a current level is to be presented next;

if the result indicates that the current response of the subject is correct and if the previous response is correct or both the previous and last-but-one responses are correct, the host computer determines that an optotype mark corresponding to visual acuity which is one level higher than the current level is to be presented next; and if the result indicates that the current response is incorrect, the host computer determines that an optotype mark corresponding to visual acuity which is one level lower than the current level is to be presented next;

a storing step of causing a memory to store at least a visual acuity level corresponding to the displayed optotype mark and the result of the determination performed in the determining step;

a timer step of determining whether a predetermined time or a predetermined number of display operations is reached, wherein when the predetermined time or the predetermined number of display operations is not reached, the computing device causes an optotype mark corresponding to the result of the response correctness/incorrectness determination to be displayed in the displaying step; and a result displaying step of causing, when the predetermined time or a predetermined number of responses is reached, the host computer to compile measurement results and transmit the measurement results to the subject's computer and causing the measurement results to be output on the display of the subject's computer.

* * * * *